United States Patent [19]

Eroyan

[11] 4,094,016
[45] June 13, 1978

[54] ARTIFICIAL HAND AND FOREARM

[76] Inventor: Gary Eroyan, 1314 N. Crawford St., Detroit, Mich. 48209

[21] Appl. No.: 746,794

[22] Filed: Dec. 4, 1976

[51] Int. Cl.² .......................... A61F 1/06; A61F 1/00
[52] U.S. Cl. .......................................... 3/1.1; 3/12.6; 3/12.7
[58] Field of Search ............................. 3/1.1, 12–12.7

[56] References Cited

U.S. PATENT DOCUMENTS

| | | | |
|---|---|---|---|
| 1,004,482 | 9/1911 | Schackelford et al. | 3/12.6 X |
| 1,285,617 | 11/1918 | Caron | 3/12.7 |
| 1,499,052 | 6/1924 | Carson | 3/12.6 |
| 1,507,682 | 9/1924 | Pecorella et al. | 3/12.7 X |
| 2,364,313 | 12/1944 | Pecorella | 3/12.7 |
| 2,553,827 | 5/1951 | Mason | 3/12.7 |
| 2,580,987 | 1/1952 | Alderson | 3/1.1 |
| 2,847,678 | 8/1958 | Opuszenski | 3/12.7 |
| 3,418,661 | 12/1968 | Allison et al. | 3/1.1 |

FOREIGN PATENT DOCUMENTS

| | | | |
|---|---|---|---|
| 821,690 | 11/1951 | Germany | 3/12.7 |
| 895,044 | 10/1953 | Germany | 3/1.1 |

Primary Examiner—Ronald L. Frinks
Attorney, Agent, or Firm—Cullen, Settle, Sloman & Cantor

[57] ABSTRACT

An artificial hand and forearm comprises an elongated housing open at its rear end adapted to receive the stub of a human forearm and adjacent upper arm, adapted for securing thereto. A plate within the housing pivotally mounts a series of finger assemblies within the housing, with said finger assemblies projecting from the housing. A thumb assembly is spaced from said finger assemblies and pivotally mounted upon said plate, with the thumb assembly projecting from the housing and opposed to the forefinger assembly. A cam shaft is journalled upon said plate and mounts a series of spaced cams respectively registering with the inner ends of the finger assemblies. One cam includes a pair of opposed cam surfaces for simultaneous registry with the forefinger and thumb assemblies. A spring biases said finger assemblies into an open position against said cams. A reversible electric motor within the housing has an output shaft geared to the cam shaft. A power source, a switch and an electrical circuit within the housing connects said motor. The switch under the control of an arm stub may be activated in one direction, said cams rotating in one direction moving said finger and thumb assemblies inwardly to grip an object, deactivating said switch stopping said fingers. Successively activating said switch in the opposite direction reversing said motor, said cams rotating in the opposite direction pivoting said thumb and finger assemblies to move outwardly releasing said object.

20 Claims, 14 Drawing Figures

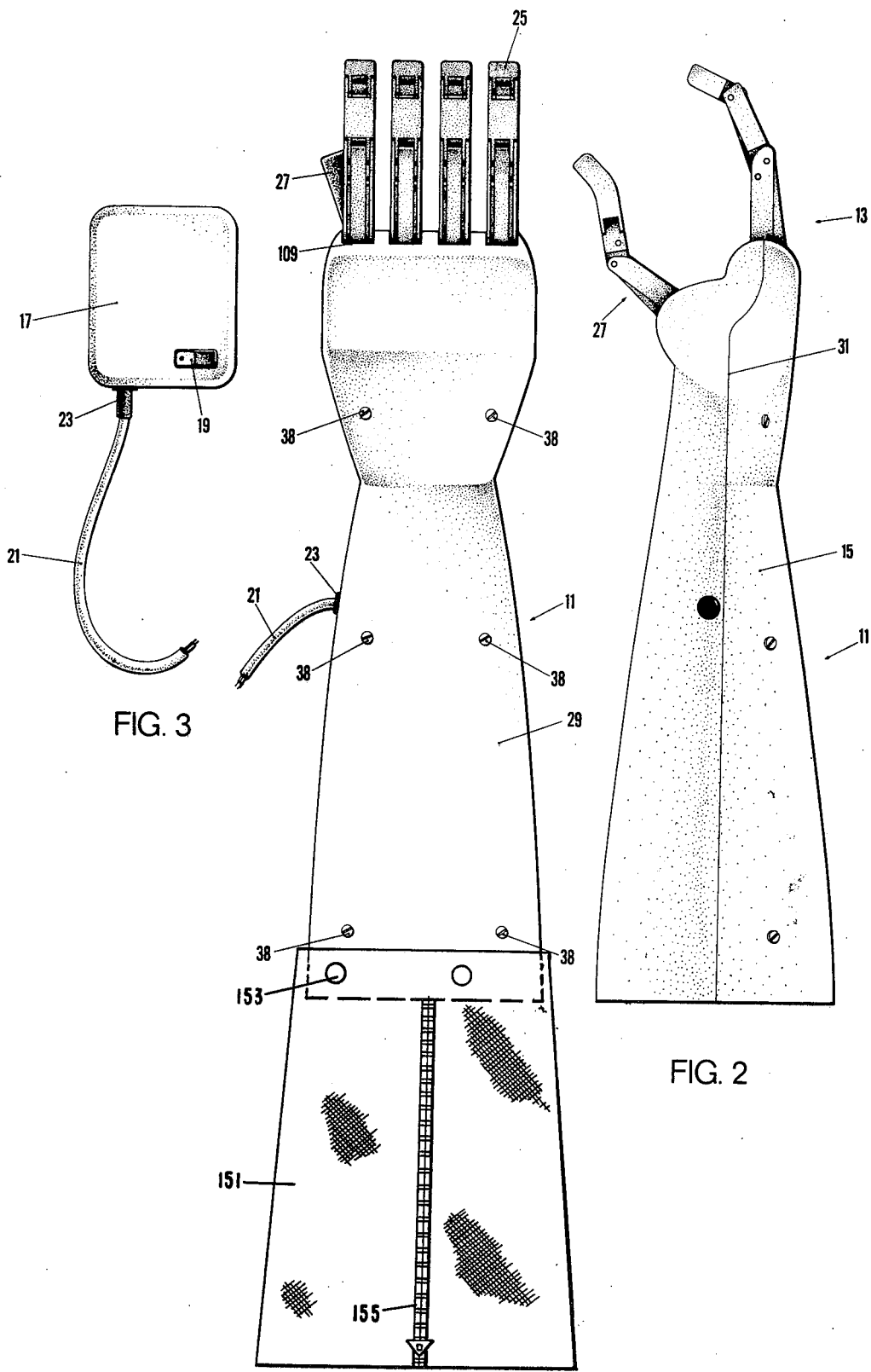

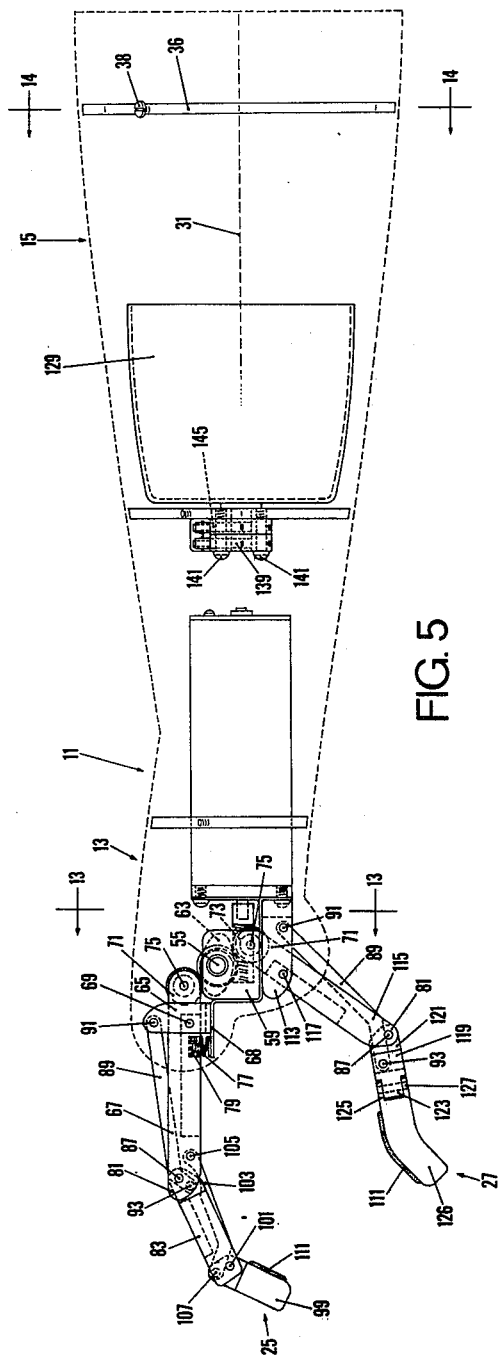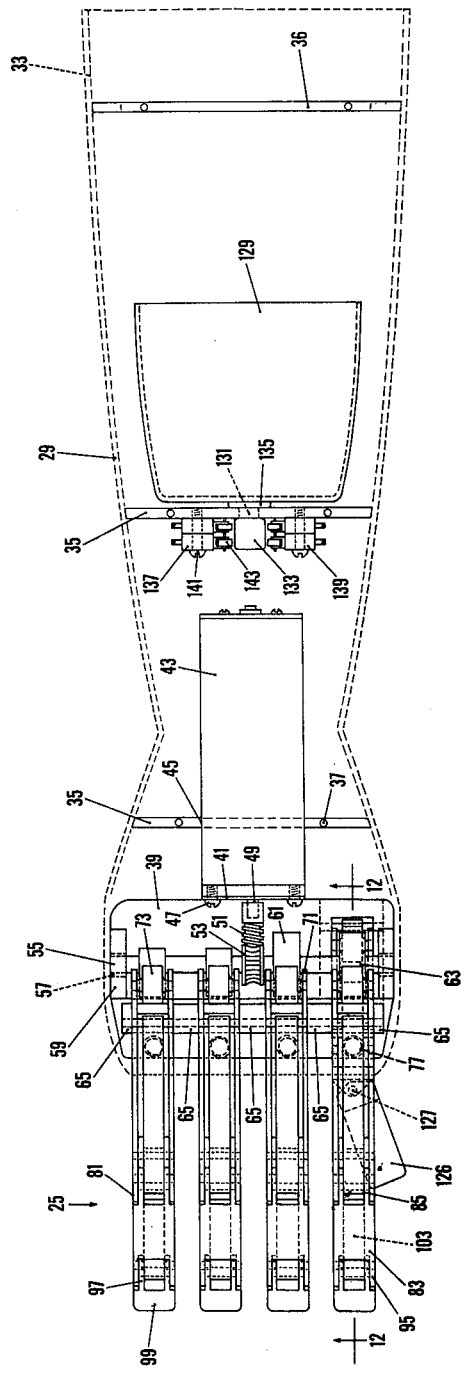

4,094,016

ARTIFICIAL HAND AND FOREARM

BACKGROUND OF THE INVENTION

Artificial hand and forearm assemblies are known in the prior art as found in one or more of the following U.S. Patents:
- 806,126: Felio
- 1,004,482: Shackelford et al.
- 1,285,617: Caron
- 2,553,827: Mason
- 2,580,987: Alderson
- 3,418,661: Allison et al.
- 3,883,900: Jerard et al.

SUMMARY OF THE INVENTION

It is an object of the present invention to provide an improved artificial hand and forearm which represents a substantial improvement and simplification over earlier prior art devices of this type and wherein the number of parts have been reduced together with a simplified operating mechanism and control. It is another object to provide an improved control mechanism for a series of human finger and thumb simulated finger and thumb assemblies. It is a further object to provide power source internal of the hand and forearm assembly with a suitable and simplified power transmission between motor output shaft and the finger assemblies and thumb assembly under the control of a switch which is operated by the stub of the arm over which the present housing is assembled.

It is a further object to provide a power pack including a housing containing one or more dry cells together with an electrical conduit to a switching mechanism within the housing. These and other objects will be seen from the following specification and claims in conjunction with the appended drawings.

THE DRAWINGS

FIG. 1 is a front elevational view of the present artificial hand and forearm shown in an upright position.

FIG. 2 is a left side elevational view thereof.

FIG. 3 is a front view of the electrical power pack.

FIG. 4 is a longitudinal plan view of the finger assemblies and power and control mechanism as assembled within the housing, the upper portion of the housing being removed for clarity.

FIG. 5 is a side elevational view thereof.

Figure 6:
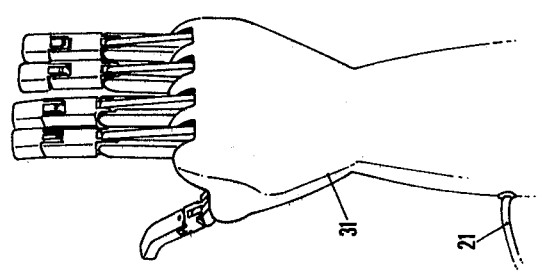
FIG. 6 is a fragmentary perspective view with the finger and thumb assemblies in normal release position.

It will be understood that the above drawings illustrate merely a preferred embodiment of the invention and that other embodiments are contemplated within the scope of the claims hereafter set forth.

DETAILED DESCRIPTION OF THE INVENTION

Referring to the drawings, the present artificial hand and forearm is generally indicated at 11 FIG. 5 which includes hand 13, forearm 15, power pack 17, FIG. 3. The power pack includes one or a plurality of dry cells or batteries nested within a housing and including a flexible insulated conduit 21 which extends through a sealing gromet 23 within the power pack housing projects into the forearm portion of the housing through a corresponding sealing gromet 23, FIG. 1. The power pack includes a manual "off" and "on" switch 19 to protect the life of the batteries. Said power pack is adapted for storing in a pocket of the user's garment.

The artificial hand includes a series of natural simulating finger assemblies 25 and opposed thereto a thumb assembly 27, FIG. 1, which project through a series of corresponding clearance slots 109 at the forward end of the hand portion of the housing as shown in FIG. 1.

Figure 7:
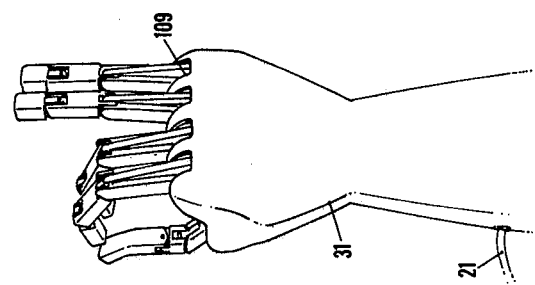
FIG. 7 is a similar view showing the forefinger and next finger assemblies and thumb assembly articulated into gripping position.
Figure 8:
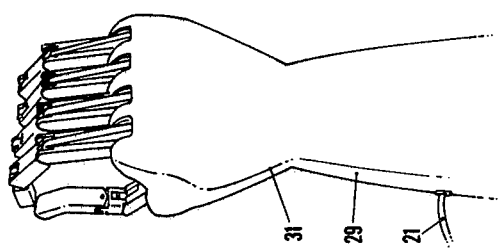
FIG. 8 is a similar view showing all finger assemblies articulated into gripping position.

The artificial hand and forearm includes a hollow elongated formed housing of a suitable plastic material, such as polystyrene or other suitable plastic which has been formed into a pair of opposing housing halves 29 which are assembled together along the longitudinal parting lines 31 such as shown in FIGS. 6, 7 and 8.

To facilitate assembly in a preferred embodiment of the invention the outer edges of the lower housing half have a laterally inset longitudinal flange for cooperative assembling registry with corresponding laterally offset outer longitudinal flanges upon the top housing half. Within the bore 33 defined by the housing halves there are provided a series of longitudinally spaced apertured partitions 35 of the general cross-sectional shape of the housing having internally threaded apertures 37, FIG. 4, adapted to receive fasteners 38 which project from the top housing half to complete the assembly of the housing.

Suitably anchored within the hand end of the housing, upon the lower half thereof is a formed mounting plate 39. Upright end flange 41 upon the rear side of mounting plate 39 extends at right angles thereto and is secured by fasteners 47 to the forward end of the electric, preferably DC motor 43 FIG. 4. Said motor is centrally disposed within said housing and is nested down within an arcuate cradle or groove 45 within partition 35 and has a central longitudinal axis which includes output shaft 49.

Spiral gear 51 is secured upon said output shaft and is in mesh with the worm 53 secured to cam shaft 55. Said shaft at its opposite ends, FIG. 4, is journaled within the bearings 57 within the bearing blocks 59 secured upon the opposite ends of the mounting plate. A series of longitudinally spaced finger operating cams 61 are secured to the cam shaft. The outer cam 63 is a double cam with cam surfaces at its opposite sides adapted for controlling simultaneously the articulation of the forefinger and opposing thumb assemblies as hereafter described.

The mounting plate 39 has an upright web which terminates in the horizontally disposed finger base plate 68, FIG. 5, which mounts a series of parallel spaced upright finger supports 65, also shown in FIG. 4.

Each of the finger assemblies 25 at their inner ends are nested within the hand portion of the housing, interposed between the corresponding pair of finger supports 65 and pivotally mounted thereon by the common transverse pivot pin 69. Accordingly each of the finger assemblies inwardly of their rear ends are pivotally mounted on the mounting plate and upon the interior of the housing.

Each of the finger assemblies includes a finger base 67. Pivot pin 69 extends stands transversely between all of the finger supports 65 into portions of the respective finger bases inwardly of their inner ends to provide such pivotal mounting for each of said finger assemblies. Each of the finger assemblies terminate in the bifurcations 71. A roller 73 is disposed within each bifurcation and journaled thereon by the transverse shaft 75 and adapted for operative engagement with the corresponding cam 61 or cam 63.

Each of the finger assemblies is biased outwardly to a normally open release position by the individual coil spring 77 which is anchored upon finger base plate 68. These springs at their free end extend into undercut sockets 79 in the undersurface of each finger base 67 of the finger assemblies biasing them to the outward release position shown in FIG. 5 with rollers 73 in engagement with the corresponding cam.

The forward end of each of the finger bases 67 is bifurcated at 81 and receives inset bifurcations 85 of the finger intermediate 83 and pivotally connected thereto at 87. Each of the finger assemblies 25 include in conjunction with the finger base 67 a control mechanism by which upon initial pivotal movement of the finger base 67 that there will be a corresponding articulation and additional pivotal movement of the intermediate 83 forming a part of the finger assembly as well as of the finger tip 99.

For this purpose there is provided for each of the finger assemblies an elongated control link 89 which at one end is pivoted to the finger supports by the pivot pin 91. The control link 89 extends over the corresponding finger base 67. The outer portion of said link is nested within a forward recessed portion of the finger base extends into the bifurcation 85 of the intermediate 83 and is pivotally connected thereto by the pivot pin 93 adjacent one end of said intermediate.

The outer end of the intermediate 83 forming a part of the finger assembly is bifurcated at 95 and is adapted to cooperatively receive the inset bifurcation 97 of fingertip 99 pivotally connected thereto at 101.

The forementioned articulating control mechanism includes a second control link 103, FIGS. 4 and 5, at one end pivotally connected to the outer end portion of finger base 67 as at 105. Said control link extends along and under the intermediate 83 and at its free end extends between the bifurcations 95 and 97 and is pivotally connected to the fingertip by the pivot 107.

Therefore the articulating control for the finger assembly includes the pair of links 89 and 103 arranged in such manner that an initial inward movement of the finger base 87 causes a corresponding but additional articulating pivotal movement of the finger intermediate 83 functioning through the control link 89, and this pivotal movement of the finger base 87 transmits additional articulating pivotal movement of the fingertip 99 by virtue of the second control link 103. It is this articulation of the respective parts of the finger assembly 67, 83 and 99 which effects an inward gripping action of the finger assembly 25 on activation of the corresponding control cam 61 or control cam 63.

In completing the construction of the finger assembly 25 upon the undersurface of the respective fingertips 99 are mounted suitable resilient pads 111 of sponge rubber or similar material to facilitate gripping an object. In connection with the mounting of the thumb assembly 27 with respect to the housing and particularly the hand end thereof there are provided as shown in FIGS. 4 and 5 a pair of parallel spaced thumb supports 113 which extend forwardly of end flange 41 of mounting plate 39.

A thumb assembly 27 includes thumb base 115 whose inner end is nested within the end housing and inwardly of its end is pivotally mounted upon the thumb supports 113 by the pivot pin 117.

Outer portions of the thumb base 115 extend outwardly of a corresponding slot 109 formed within the lower half of the housing 29. The outer end of the thumb base 115 includes a bifurcation 81 which receives therein the corresponding inset bifurcation 121 of the thumb intermediate 119 and is pivotally connected thereto as at 87, FIG. 5.

Boss 123 at the outer end of the thumb assembly intermediate 119 cooperatively receives the bifurcation 125 at the inner end of the thumbtip 126, and is pivotally connected thereto by the pivot pin 127. Pivot 127 is arranged transversely to pivot 87 whereby the fingertip 126 is adapted for lateral inward and outward movements with respect to the thumb intermediate portion 119. The interior surface of the thumbtip 126 is also covered with a resilient pad 111 providing an improved frictional grip with respect to the corresponding pad 111 on the forefinger shown in FIG. 5.

Accordingly the thumb assembly 27 includes the thumb base 115 and aligned therewith the thumb intermediate portion 119 pivoted thereto at 87 and in substantial alignment therewith the thumbtip 126.

For proper articulation of the respective parts of the thumb assembly, there is additionally provided a control link 89 similar to the control link 89 previously described with respect to the finger assemblies which at its inner end is pivotally mounted as at 91 upon the thumb supports 113. The forward end portion of the control link 89 extends between the bifurcations 81 and 121 and is pivotally connected to the intermediate 119 as by the pivot pin 93. Accordingly pivotal movements of the thumb base 115 under the control of the cam 63 will cause additional articulating pivotal movement of the thumb intermediate portion 119 and the fingertip 126 mounted thereon.

A second transverse partition 35 within the housing halves 29 mounts the axially directed arm stub control cup 129 whose axial shaft 131 is journaled and supported through said later partition 35 and mounts the upright switch control cam 133, FIGS. 4 and 5, with a suitable spacer 135 interposed between said cup and partition.

A pair of electrical switches 137 and 139 are secured by fasteners 141 upon the opposite side of said partition. These switches include pivotal contact arms 145 which terminate in rollers 143 for the respective switches and arranged upon opposite sides of cam 133.

Figure 9:
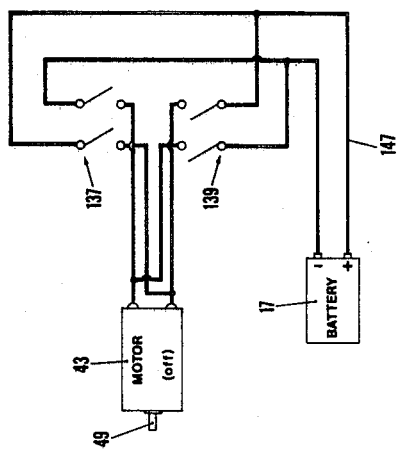
FIG. 9 is a wiring diagram with battery, motor and switch with electrical circuit open.
Figure 10:
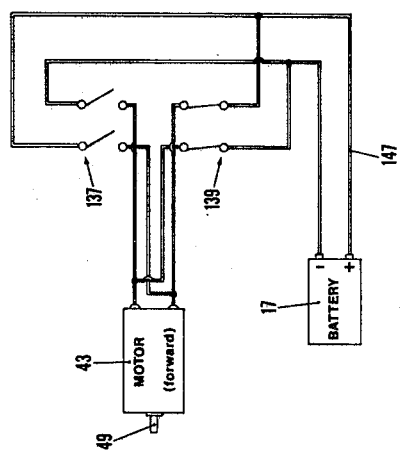
FIG. 10 is a similar view with one of the pair of switches closed to cause the motor to rotate in a forward direction.
Figure 11:
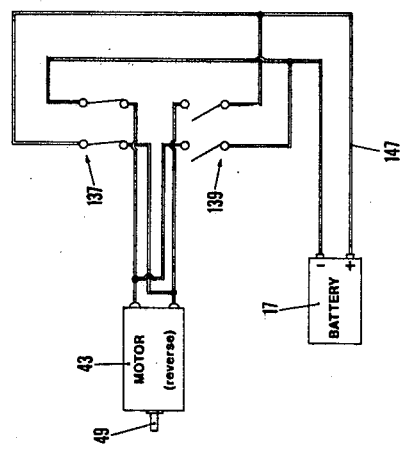
FIG. 11 is a similar view with the other of the pair of the switches closed activating the motor and its output shaft in a reverse direction.
Figure 14:
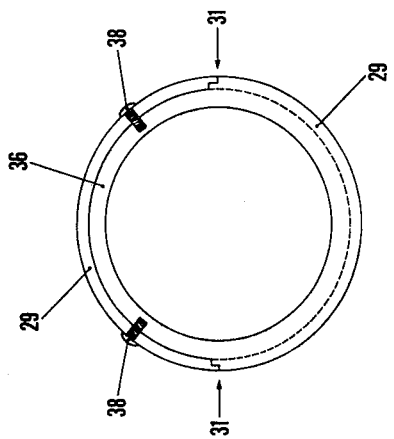
FIG. 14 is an end view taken in the direction of arrows 14—14 of FIG. 5.
Figure 13:
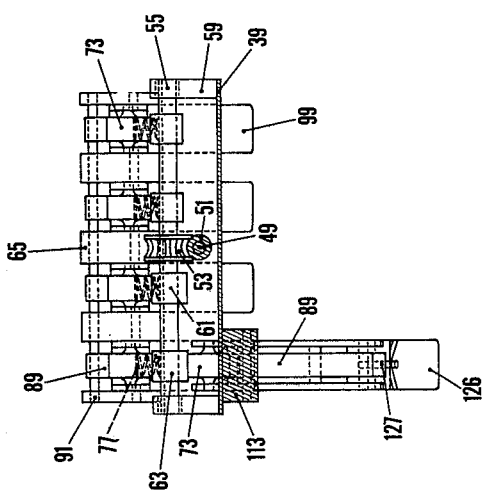
FIG. 13 is a fragmentary view taken in the direction of arrows 13—13 of FIG. 5, on an increased scale.
Figure 12:
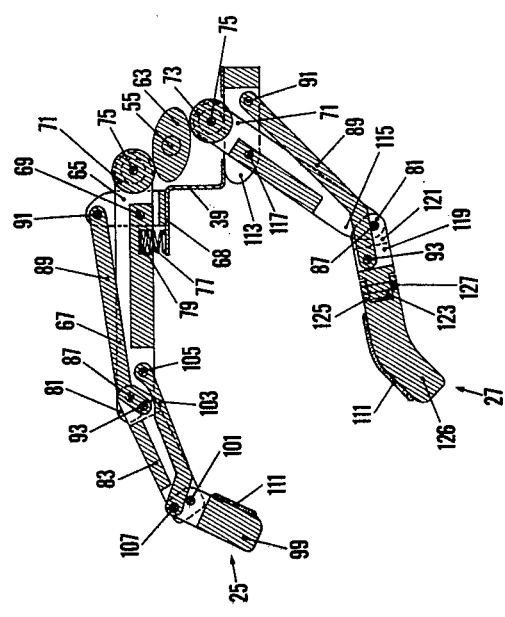
FIG. 12 is a fragmentary section on an enlarged scale taken in the direction of arrows 12—12 of FIG. 4.

Due to the formation of the cam 133 rotation of the cup 129 a short distance under the control of the arm stub inserted snugly therein for example, moves the rollers 143 of the corresponding contact arms toward switch 137 which is connected to the electric DC motor 43 as shown in FIGS. 9, 10 and 11. The cam 33 has an upright "off" position. Accordingly for illustration if the control cup 129 is rotated clockwise a short distance it will activate the switch 137 energizing the motor 43 and rotating output shaft 49 in one direction. The motor is deenergized when the cup 129 is manually returned by the arm stub to the central "off" position. If the cup 129 as viewed in FIG. 4 is rotated from this "off" position in a counterclockwise direction the cam will engage the corresponding rollers 143 and the contact arms 145 of switch 139 to close that switch and energize motor 43 and rotating shaft 49 in the opposite direction.

Referring to the drawings 9, 10 and 11 a suitable electric circuit is schematically shown at 147 which interconnects the power source namely the battery or batteries 17 with the switches 137 and 139 and to the motor 43. In the preferred embodiment this motor is a low voltage DC motor which is easily controlled into activation of one switch 137. This will drive its output shaft 49 in one direction and on activation of the other switch will drive the output shaft in the opposite direction.

In FIG. 9 the motor is de-energized, both switches 137 and 139 are open and the control cam 133 is in a central "off" position.

In FIG. 10, the control cam 133 has been rotated by the cup 139 in such manner as to close the switch 139 energizing the motor and causing the output shaft 49 to rotate in a forward direction or a clockwise direction. As the cam shaft begins to rotate, double cam 63 and the adjacent cam 61 operatively engage index finger and adjacent finger as well as the thumb assembly. Their parts articulate towards the position shown in FIG. 7. Assuming that only the two fingers are necessary for gripping an object such as a pencil as in FIG. 7. By returning the cam 133 to the "off" position the inward movement of the finger assemblies and thumb assembly of FIG. 7 is interrupted. FIG. 6 shows the normal open positioning of the finger assemblies and thumb assemblies.

Should it be desired however to effect an articulation of the additional finger assemblies this is accomplished by permitting the cam 133 to remain in the "on" position for an additional period so that the successive cams 61 for the remaining two fingers, which have a timed relation with respect to the first mentioned cams, are effective for rotating the other fingers such as to the gripping position shown in FIG. 8 with all finger assemblies articulated inward with respect to the inwardly articulated thumb assembly.

In order to return the finger assemblies and thumb assembly to the position shown in FIG. 6 it is necessary that the control cam 133 be rotated in the opposite direction thus causing a reversal of the direction of rotation of output shaft 49 of the motor. This will cause the respective cams 61 and 63 to return to the initial position with the springs 77 being effective for biasing the finger assemblies back to open object release position. The thumb assembly opens by gravity.

As shown in FIG. 5, rearwardly of the partitions 35, there is provided a third arcuate support member 36 whose free ends rest upon and are secured to the lower housing one half 29 in order to receive the stub end of the crippled arm. The respective upper housing half 29 overlies the arcuate support 36 and is secured thereto by similar fasteners 38 best shown in FIG. 1.

An assembly and mounting sleeve 151, FIG. 1, of fabric material, at one end is snap-fastened at 153 over the rear end of housing 29. The sleeve is slit longitudinally to provide a pair of free edges which are interconnected by zipper 155. The zipper is closed after the sleeve is assembled over the upper arm of the user.

I claim:

1. An artificial hand and forearm comprising a hollow elongated formed housing of the general shape of the forearm and hand having a longitudinal axis and open at its rear end adapted to receive the stub end of the human forearm;

with portions of the housing adapted to receive the corresponding upper arm and adapted for securing thereto;

the housing at its front end having a series of thumb and finger apertures therein;

a mounting plate anchored within the hand end of the housing;

a series of elongated finger assemblies including a forefinger assembly adjacent their one ends nested within the hand end of the housing, and inwardly of said one ends pivotally mounted upon said plate upon a transverse axis;

the other ends of said finger assemblies projecting axially through said finger apertures;

a thumb assembly spaced from said finger assemblies, adjacent one end nested within the hand end of said housing, and inwardly of its end pivotally mounted upon said plate upon a transverse axis;

the other end of the thumb assembly projecting axially through said thumb aperture and opposed to the forefinger assembly;

a rotatable camshaft at its ends journaled upon said plate on a transverse axis and spaced from said finger and thumb assemblies;

a series of spaced cams secured upon said shaft respectively registering with the inner ends of said finger and thumb assemblies;

one cam having a pair of opposed cam surfaces for registry with forefinger and thumb assemblies;

means biasing said finger assemblies into an open position against said cams;

a reversible electric motor within said housing having an axial output shaft;

gear means interconnecting said cam shaft and output shaft;

a power source;

a switch means within said housing; and an electrical circuit interconnecting said power source, switch means and motor;

whereby the switch means under the control of said arm stub may be activated in one direction for a short period, said cams rotating in one direction moving said finger and thumb assemblies inwardly toward an object gripping position;

deactivating said switch means stopping said fingers to hold said object;

successively activating said switch for a short period in the opposite direction reversing said motor, said cams rotating in the opposite direction permitting said thumb and finger assemblies to move toward a release position, releasing said object, deactivating said switch stopping said fingers in an open position.

2. In the artificial hand of claim 1, said housing including opposed upper and lower transversely concave sections;

one section having an upstanding internal flange throughout its length on opposite sides;

the other section having a corresponding outer depending flange laterally interlocked with said internal flange;

a series of transverse apertured spacers secured to one of said housing sections;

and means fastening the other housing section to said spacers.

3. In the artificial hand of claim 1, an assembly and mounting sleeve of fabric material at one end snap fastened over the rear end of said housing;

one side of said sleeve being longitudinally slit to provide a pair of free edges;

and a zipper interconnecting said free edges adapted to facilitate assembly over and securing to the upper arm of the user.

4. In the artificial hand of claim 1, the mounting of said finger assemblies including a series of laterally aligned parallel finger supports on said mounting plate;

each finger assembly being nested between a pair of said supports; and a pivot pin extending through all of said supports and finger assemblies.

5. In the artificial hand of claim 4, the mounting of said thumb assembly including a pair of parallel thumb supports on said mounting plate spaced from said finger supports;

said thumb assembly nested between said thumb supports and pivotally mounted thereon.

6. In the artificial hand of claim 1, the inner ends of said thumb and finger assemblies being bifurcated;

and a cam roller journaled between the bifurcations of each finger and thumb assembly and registering with said cams respectively.

7. In the artificial hand of claim 1, said biasing means including a series of coil springs mounted upon said plate and bearing against each of said finger assemblies.

8. In the artificial hand of claim 1, each finger assembly and thumb assembly including an elongated base adjacent to one end pivotally mounted upon said mounting plate;

an intermediate aligned with said base at one end pivotally connected thereto; and a fingertip aligned with said intermediate, at one end pivotally connected thereto;

said base, intermediate and tip assembly simulating the human fingers and thumb.

9. In the artificial hand of claim 8, the adjacent ends of said base, intermediate and tip being bifurcated, with the bifurcations overlapping; and pivot pins interconnecting said bifurcations.

10. In the artificial hand of claim 9, control means between said mounting plate and intermediate and between said finger base and finger tip, whereby pivotal movement of said finger base effects corresponding pivotal movements of said intermediate and finger tip, for progressive articulation of said intermediate and said finger tip.

11. In the artificial hand of claim 10, said control means including an elongated link pivotally anchored at one end to the mounting plate and at its other end pivotally connected to one end of said intermediate; and a second link at one end pivotally connected to said finger base at its outer end, the other end of said second link pivotally connected to said fingertip.

12. In the artificial hand of claim 1, said gear means including a first gear secured on said output shaft and a second gear secured upon said cam shaft, in mesh with said first gear.

13. In the artificial hand of claim 12, said first gear being a spiral gear, and said second gear being a worm gear.

14. In the artificial hand of claim 1, said power source including a power pack housing including at least one dry cell battery, said power pack adapted for storing in a pocket of the users garment; and a flexible electrical conduit interconnecting said power pack and said switch means.

15. In the artificial hand of claim 1, a transverse apertured partition within a rearward portion of said housing;

said switch means being mounted on said partition;

a rearwardly opening control cup journaled upon said partition and connected to said switch means, the arm stub of the user adapted to snugly fit within said cup for selectively rotating said cup to the right or left of an "off" position for energizing said motor for selective rotation of its output shaft in two directions;

rotation in one direction until stopped causing said finger and thumb assemblies to move toward each other; and rotation in the other direction causing said finger and thumb assemblies to move away from each other.

16. In the artificial hand of claim 15, said switch means including a pair of normally open switches respectively connected to said motor for effecting rotation of its output shaft in one of two directions;

a rotatable cam between said switches and connected to said cup, said cam on movement in one direction adapted to activate one of said switches energizing said motor for rotation in one direction and upon return to normal "off" position of said cam deactivate said motor;

said cam on movement in the other direction adapted to activate the other of said switches energizing said motor for rotation in the opposite direction and upon return to normal "off" position of said cam deactivating said motor.

17. In the artificial hand of claim 8, the pivotal connections of said finger base, intermediate and tip, and the pivotal connection between said thumb base and intermediate being upon transverse parallel axes.

18. In the artificial hand of claim 17, the pivotal connection between the thumb tip and intermediate being transverse to the pivotal connection between said intermediate and thumb base.

19. In the artificial hand of claim 10, said control means including an elongated link pivotally anchored at one end to the mounting plate and at its other end pivotally connected to one end of said intermediate; and a second link at one end pivotally connected to said finger base at its outer end;

the other end of said second link pivotally connected to said fingertip;

the pivotal mounting of the elongated link and mounting plate for all of said finger assemblies including a single pin extending between all of said finger supports and said links.

20. In the artificial hand of claim 1, the cams for the forefinger and adjacent finger assemblies being advanced in a timed relation to the other pair of cams, whereby activation of said motor will initially articulate and stop only the forefinger and the adjacent finger assemblies relative to said thumb assembly;

additional activation of said motor and output shaft in the same direction providing successive articulation of the other two finger assemblies.

* * * * *